United States Patent [19]
Gorsuch et al.

[11] Patent Number: 5,242,382
[45] Date of Patent: Sep. 7, 1993

[54] APPARATUS AND METHOD FOR DIRECT MEASUREMENT OF BLOOD PARAMETERS

[75] Inventors: Reynolds G. F. Gorsuch, Yountville; John Atkin, Corona Del Mar, both of Calif.; Tommy G. Cooper, Friendswood, Tex.

[73] Assignee: Healthdyne, Inc., Atlanta, Ga.

[21] Appl. No.: 570,002

[22] Filed: Aug. 20, 1990

Related U.S. Application Data

[63] Continuation-in-part of Ser. No. 229,007, Aug. 5, 1988, Pat. No. 4,950,224.

[51] Int. Cl.$^5$ .................. A61M 37/00; A61M 1/14
[52] U.S. Cl. ............................... 604/4; 604/6; 422/44
[58] Field of Search ........................ 604/4-6, 604/48; 422/44, 101

[56] References Cited

U.S. PATENT DOCUMENTS

| | | |
|---|---|---|
| Re. 31,688 | 9/1984 | Popovich . |
| 4,240,907 | 12/1980 | Bentley . |
| 4,389,363 | 6/1983 | Molthop . |
| 4,498,990 | 2/1985 | Shaldon . |
| 4,559,034 | 12/1985 | Kirita . |
| 4,563,170 | 1/1986 | Aigner . |
| 4,583,969 | 4/1986 | Mortensen . |
| 4,604,208 | 8/1986 | Chu . |
| 4,623,327 | 11/1986 | Mahurkar . |
| 4,631,053 | 12/1986 | Taheri . |
| 4,767,400 | 8/1988 | Miller . |
| 4,769,037 | 9/1988 | Midcalf . |
| 4,776,837 | 10/1988 | Koop ........................ 604/4 |
| 4,790,331 | 12/1988 | Okada . |
| 4,820,261 | 4/1989 | Schmoll . |
| 4,844,871 | 7/1989 | Polaschegg .................. 604/6 |
| 4,850,958 | 7/1989 | Berry . |
| 4,854,322 | 8/1989 | Ash et al. ................... 604/48 |

FOREIGN PATENT DOCUMENTS 2606642 5/1988 France .
2616666 12/1988 France .

*Primary Examiner*—Randall L. Green
*Assistant Examiner*—R. Clarke
*Attorney, Agent, or Firm*—Jones, Askew & Lunsford

[57] ABSTRACT

Continuous or periodic measurement of blood gas parameters and blood pressure by separating plasma from blood and then using that plasma to measure the blood parameters. Plasma is separated from blood in vivo with a filter implanted within a blood vessel, and the separated plasma is removed to extracorporeal apparatus for analyzing blood gas parameters or measuring blood pressure. The use of plasma is equivalent to the use of whole blood for measuring blood gas parameters as the gas parameters reside in the plasma, not in the separated blood cells which remain in the blood vessel. This arrangement permits the continuous measurement of blood gases without removal of blood from the body.

14 Claims, 1 Drawing Sheet

APPARATUS AND METHOD FOR DIRECT MEASUREMENT OF BLOOD PARAMETERS

CROSS-REFERENCE TO RELATED INVENTION

This is a continuation-in-part of Ser. No. 229,007 filed Aug. 5, 1988, U.S. Pat. No. 4,950,224.

FIELD OF INVENTION

This invention relates in general to measurement of blood parameters, and relates in particular to measurement of arterial or venous blood gases and blood pressure.

BACKGROUND OF THE INVENTION

Critically ill patients who are hospitalized and in either surgery or in intensive care wards often require continuous or periodic measurement of their arterial or venous blood gases and direct blood pressure. These measurements are used by the physician to assess the status of the patient's cardiopulmonary and metabolic systems. For purposes of accuracy and time dynamics, these measurements are made continuously or repeatedly with short periods of time between measurements. Current methods and measurement sensors require a direct interface between blood and the sensor.

In the case of the blood gases, which are $PaCO_2$ (partial pressure of arterial carbon dioxide), $PaO_2$ (partial pressure of arterial oxygen) and pH (hydrogen ion content), a needle and syringe is used to penetrate a peripheral artery (usually the radial or brachial) and a sample of blood (nominally 0.5 to 1 ml) is withdrawn. The sample is injected into the sample chamber of a commercial blood gas machine which exposes the blood to a series of electro-chemical sensors and displays the sensed values on the analyzer readout. Withdrawing a continuous series of blood from the body in order to obtain a continuous reading has never proved practical because of the trauma to blood cells experienced when blood is removed from the body and the tendency of the blood to clot and clog such systems. Also, in many patients the continuous withdrawal of blood or blood samples will bleed the patient beyond a safe level.

In the case of direct blood pressure, a fluid path is normally obtained by installing a small open plastic catheter into the appropriate artery via an introducer needle and guide wire technique (Seldinger method) or with a split needle (Luther method). The catheter is attached to a fluid line which is connected to the dome of a pressure transducer and vented to atmosphere during zeroing of the transducer. This fluid path is also connected to a continuous saline drip through the fluid system into the blood to keep the fluid path from clotting and thus degrading or destroying the pressure reading. Alternately, the fluid path is periodically flushed to dislodge any blood which may be clogging the catheter.

SUMMARY OF INVENTION

The present invention permits the continuous measurement of blood gases without removing blood from the body, and without the subsequent trauma to blood cells and consequent malfunction of the blood flow path. The invention also permits the direct measurement of blood pressure without the dangers of clotting and consequent equipment malfunction.

Stated in general terms, the present invention recognizes that the use of plasma is equivalent to the use of whole blood when measuring certain parameters of blood. For example, the determinants for certain blood gas parameters such as $PaCO_2$, $PaO_2$, and pH reside in the plasma, not in the separated blood cells. Likewise, the pressure of plasma in a fluid path connected to arterial or venous blood at any instant is substantially the same as that in the blood. According to the present invention, plasma is separated and removed from the bloodstream and is subjected to analytical procedures for determining various blood gas parameters and blood pressure. The plasma then is returned to the body. Because whole blood does not leave the body, the problems associated with blood trauma and clotting in existing continuous measurement of blood gas and blood pressure are avoided.

Stated in somewhat greater detail, plasma is separated in vivo from other blood components through a membrane implantable in a blood vessel and functioning as a filter to admit plasma while preventing other blood components from passing through the membrane. The plasma thus separated in vivo by the membrane next is removed from the body and analyzed to determine one or more blood parameters. The plasma then is returned to the body. Plasma flow from the body through analysis and return takes place continuously in real time.

In vivo separation of plasma preferably is accomplished by an indwelling catheter implantable in a blood vessel and comprising one or more microporous hollow fibers. These fibers have a pore size sufficient to admit plasma while preventing other blood components from entering the hollow interior of the fiber. The separated plasma flows to the exit lumen of a catheter which removes the plasma from the body for extracorporeal analysis. The plasma then is returned to the body, preferably through another lumen of the catheter, to reenter the bloodstream.

Accordingly, it is an object of the present invention to provide an improved apparatus and method for measurement of blood parameters.

It is another object of the present invention to provide an apparatus and method for measurement of blood gases without removal of blood from the body.

It is another object of the present invention to provide an apparatus and method for the continuous measurement of blood gases without removal of blood from the body.

It is a further object of the present invention to provide an apparatus and method for direct measurement of blood pressure without removal of blood from the body.

It is still another object of the present invention to provide an apparatus and method for the continuous measurement of blood parameters without trauma to the blood and without the danger of clotting and consequent malfunction of the measurement apparatus.

Other objects and advantages of the present invention will become more readily apparent from the following description of a preferred embodiment.

DETAILED DESCRIPTION OF PREFERRED EMBODIMENT

Figure 1:
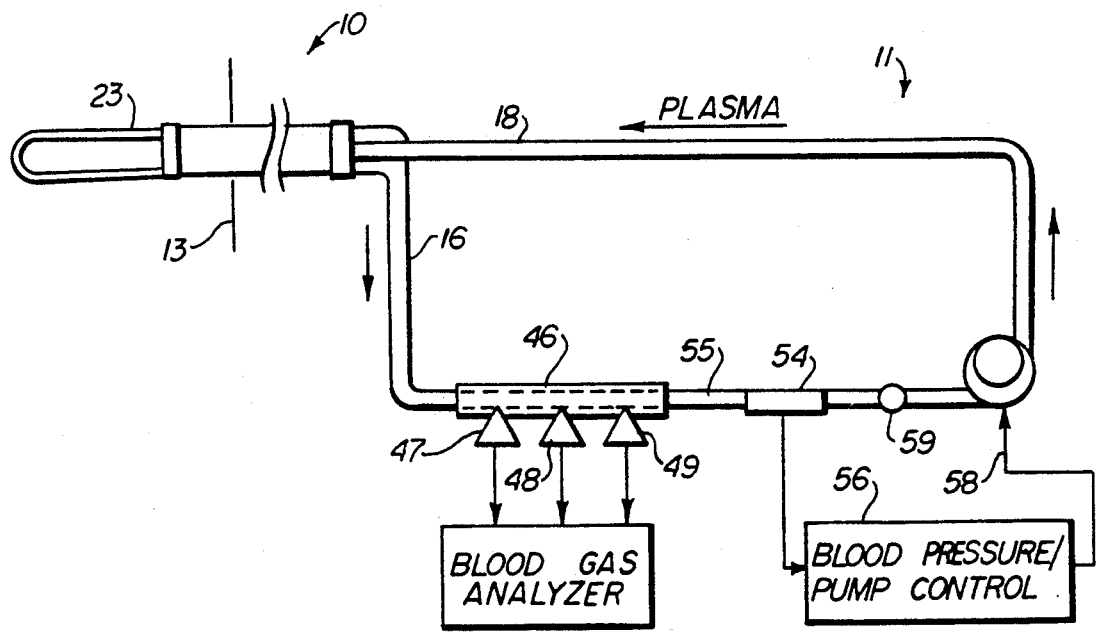
FIG. 1 is a schematic view showing a preferred embodiment of the present invention, including an apparatus for in vivo separation of plasma and apparatus for continuous analysis of the separated plasma.

FIG. 1 shows apparatus for direct measurement of blood parameters including a plasma separation catheter 10 for separating plasma from whole blood, and the measurement apparatus 11 for measurement of blood parameters from the separated plasma. The plasma separation catheter 10 functions as a filter to separate plasma from the cellular products of blood flowing through a vein or artery, with 13 schematically illustrating one wall of such a blood vessel in a patient. The plasma separated from the blood leaves the catheter 10 through the plasma exit tube 16 connected to the analysis apparatus 11, and a plasma return tube conducts the plasma from the analysis apparatus back to the catheter 10 where the plasma is reintroduced to the patient's bloodstream within the blood vessel 13. A pump 19, preferably a peristaltic pump or the like, provides positive displacement of the plasma from the analysis apparatus to the plasma return tube 18.

Figure 2:
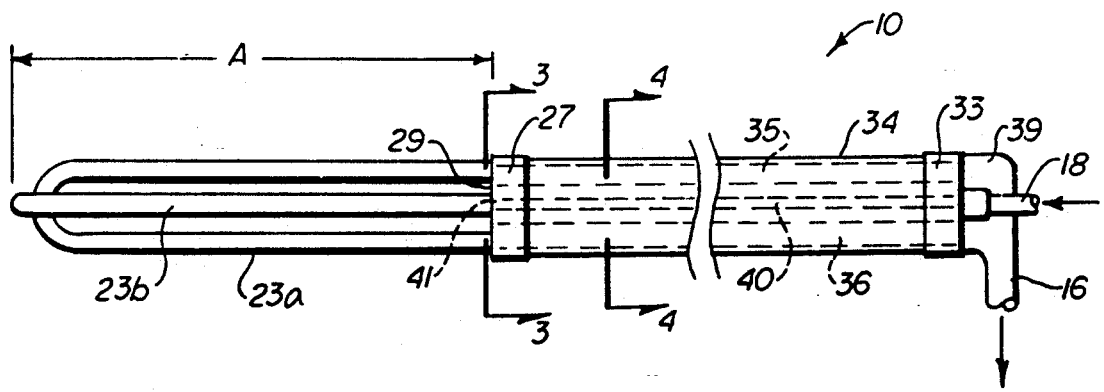
FIG. 2 is an enlarged pictorial view showing the in vivo plasma separation apparatus of FIG. 1.

Details of the plasma separation catheter 10 are shown in FIG. 2. The in vivo plasma separation catheter 10 comprises at least one hollow microporous fiber 23 having a hollow interior disposed longitudinally therein. The fibers 20 can be made of any suitable material such as polymeric plastic, but are preferably polymeric polypropylene. The fibers 20 can be made by methods known to those skilled in the art. For example, polypropylene can be mixed with a solvent and the mixture spun; as the solvent and polymer phase are separated the fiber is formed. One suitable fiber commercially available is Plasmaphan ® membranes made from polypropylene polymer (ENKA AG, Wuppertal, West Germany).

The fibers 20 possess a microporous structure having a very high void volume, low variation in pore distribution, and high reproducibility in production. The fiber pore size is sufficient to admit plasma to pass through the wall of the hollow fiber and into the hollow center of the fiber, although the overall size of the fibers should not significantly obstruct fluid flow through the blood vessel. Cellular components of the blood, however, are unable to diffuse through the fiber pores. Predominantly large molecuels will pass around the apparatus 10 within the vein fluid flow. The vein fluid flow also prevents clogging of the pores. The fiber pore size can be from about 0.1 to 1.0 $\mu$m; preferably, from about 0.2 to 0.8 $\mu$m; and more preferably, from about 0.4 to 0.6 $\mu$m.

Modern gas analyzer sensors of the kind used in the measurement apparatus 12, and described below in greater detail, require only 0.5 ml of sample fluid to make a measurement and have a time constant of less than one minute. Therefore, a plasma separation catheter which has a capacity of 0.5 ml per minute is adequate to provide continuous measurements. Under these conditions the plasma separation catheter requires one square centimeter of surface area to provide the needed flow rate of plasma. Thus, a preferred embodiment of the plasma separation catheter 10 has a fiber length of 13.2 cm, with the fiber having an outer diameter of 240 microns and a 40 micron wall thickness. The preferred configuration of this fiber is in two looped segments 23a and 23b each having a nominal length A of 3.4 cm.

Figure 3:
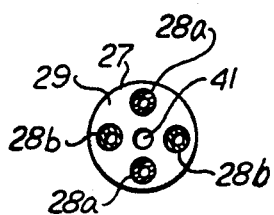
FIG. 3 is a section view taken along line 3—3 of FIG. 2.
Figure 4:
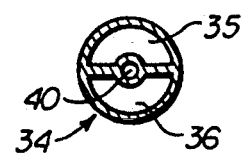
FIG. 4 is a section view taken along line 4—4 of FIG. 2 and axially rotated with respect to FIG. 3.

The looped segments of fiber 23a and 23b are longitudinally aligned in a generally parallel orientation and extend outwardly from the distal header 27 forming part of the plasma separation catheter. The ends of the fibers are connected to the distal header 27 by potting techniques. Referring to FIG. 3, it is seen that the two ends 28a, 28a of the fiber 23a are displaced approximately 180° apart on the outward face 29 of the distal header 27. The two ends 28b, 28b of the fiber 23b are likewise positioned on the outer face 29, and are offset 90° from the ends of the fiber 23a.

The distal header 27 connects to the proximal header 33 of the plasma separation catheter 10 by a triple lumen catheter 34. The two outer lumens 35 and 36 are angularly aligned for flow communication with the ens 28a, 28a and 28b, 28b, respectively, of the fibers 23a and 23b. The outer lumens 35 and 36 thus provide dual plasma flow passages extending from both ends of the hollow fibers 23a and 23b and through the proximal header 33 to the plasma exit manifold 39, which connects to the plasma exit tube 16.

The central lumen 40 of the catheter 34 also extends between the distal header 27 and the proximal header 33. The plasma return tube 18 connects to the central lumen 40 at the proximal header 33 and provides a return path for plasma from the measurement apparatus 12. The central lumen 40 at the distal end connects to the coaxial opening 41 of the distal header 27. This opening 41 extends through the distal header 27 and opens onto the outward face 29 of that header, into flow communication with a blood vessel in which the plasma separation catheter 10 is implanted.

The portion of the plasma separation catheter 10 inserted into the blood vessel, schematically indicated by the wall 13, FIG. 1, includes the active elements made up of the fibers 23a, 23b and the distal header 27. The catheter including the distal header 27 is sized to a 20 gage needle which will fit inside an 18 gage Luther split introducer needle. The catheter is installed into the appropriate blood vessel using a percutaneous technique.

Further details of the implantable-catheter for in vivo separation of plasma from blood are described in detail in U.S. Pat. No. 4,950,224, which is incorporated herein by reference.

The analysis apparatus 11 shown in FIG. 1 includes a cuvette 46 connected to receive the plasma flowing through the plasma exit tube 16 from the catheter 10. The cuvette provides a fluid path exposing the plasma to the blood gas sensors 47, 48, and 49 which measure $PaCO_2$, $PaO_2$, and pH, respectively, and send signals for those measured values to the blood gas analyzer 50. A readout of the values for these blood gas parameters is provided by the blood gas analyzer 50. The analyzer 50 may be any of the sensors 47, 48, and 49 preferably are optical blood gas parameter sensors such as the sensors manufactured by Cardiovascular Devices, Inc. or by Optical Sensors for Medicine, Inc. The nature and operation of such sensors is known to those skilled in the art and need not be detailed herein.

After the plasma passes through the cuvette 46, it passes through the pressure measurement dome of a blood pressure sensor 54. The pressure in the fluid path 55 leading to the blood pressure sensor 54 at any instant is the same as that in the blood vessel in which the plasma separation catheter 10 is implanted, although some high-frequency "ringing" pressure components are filtered by the porous membrane of the fiber 23, which eliminates the need for an extrinsic signal filter performing that purpose. The blood pressure signal from the transducer 54 goes to the blood pressure readout device 56, which also provides flow control signals on the line 58 to operate the pump 19 which returns plasma to the body by way of the plasma return tube 18 and the central lumen 40 of the catheter 34. A sample port 59 is connected in the plasma flwo line between the blood pressure sensor 54 and the pump 19 to take plasma samples used for other assays, for example, blood glucose measurement.

It should be understood that the foregoing refers only to a preferred embodiment of the present invention and that numerous modifications and changes thereto may be made without departing from the spirit or scope of the invention as defined in the following claims.

What is claimed is:

1. An apparatus for measuring at least one parameter of blood flowing in an organism, comprising:
    at least one elongated microporous fiber having a hollow interior, said fiber being dimensioned to be received within a blood vessel of the organism without significantly obstructing fluid flow through the blood vessel;
    the pore size of the fiber being sufficient to allow plasma to diffuse through the pores into the hollow interior of the fiber but not sufficient to allow cellular components larger than plasma to diffuse therethrough, so as to accomplish in vivo separation of plasma from blood;
    the hollow interior of said elongated fiber being in fluid communication with a means for conducting plasma comprising a first hollow tube which connects to the hollow interior of the fiber and permits passage of plasma from the fiber, and a second hollow tube which returns plasma to said blood vessel;
    extracorporeal means responsive to a predetermined parameter of the plasma passing through the first tube for producing a signal indicative of the parameter; and
    means conducting the plasma from the extracorporeal means to the second hollow tube for return to the blood vessel.

2. Apparatus as in claim 1, wherein the last-mentioned means comprises a pump for moving the plasma from the extracorporeal means to the second hollow tube.

3. Apparatus as in claim 1, wherein the fiber is composed of a polymeric material having a pore size of from about 0.1 to 1.0 $\mu$m.

4. Apparatus as in claim 1, wherein the fiber is composed of a polymeric material having a pore size of about 0.2 to 0.8 $\mu$m.

5. Apparatus as in claim 1, wherein the fiber is composed of a polymeric material having a pore size of about 0.4 to 0.6 $\mu$m.

6. Apparatus as in claim 1, wherein the extracorporeal means comprises a cuvette connected to receive the extracorporeal flow of plasma; and
    sensor means responsive to the plasma flowing through the cuvette to measure the parameter.

7. Apparatus as in claim 6, wherein the sensor means comprises a plurality of sensors responsive to a corresponding plurality of blood gas parameters in the plasma flowing through the cuvette.

8. An apparatus for measuring at least one parameter of blood flowing in an organism, comprising:
    a filter comprising at least one elongated microporous fiber having a hollow interior and dimensioned to fit within a blood vessel;
    the pore size of the fiber being sufficient to allow plasma to diffuse through the pores into the hollow interior but not sufficient to allow cellular components larger than plasma to diffuse therethrough, so as to accomplish in vivo separation of plasma from blood;
    means comprising a first hollow tube connected to the filter to conduct the plasma from the interior of the fiber to an extracorporeal location;
    a sensor at the extracorporeal location and operatively associated with the plasma to measure a predetermined blood parameter of the plasma; and
    means comprising a second hollow tube connected to return the plasma from the extracorporeal location to a blood vessel of the body from which the plasma was removed.

9. The apparatus as in claim 8, wherein:
    the primary filter includes a header dimensioned to fit within the first-mentioned blood vessel without substantially obstructing fluid flow through the blood vessel;
    the fiber extends outwardly from the header within the blood vessel;
    the first hollow tube is in fluid flow communication with the header to remove the plasma from the blood vessel; and
    the second hollow tube is in fluid flow communication with the header to return the plasma from the extracorporeal location to said blood vessel.

10. The apparatus as in claim 8, wherein:
    the sensor comprises a cuvette connected to receive the extracorporeal flow of plasma; and
    a plurality of optical sensor means exposed to the plasma flowing through the cuvette and operative to determine certain blood gas parameters of the plasma.

11. The apparatus as in claim 8, wherein the fiber has a pore size of about 0.1 to 1.0 $\mu$m.

12. An apparawtus for measuring at least one value of blood gas in blood flowing in an organism, comprising:
    a primary filter comprising a microporous membrane dimensioned to be received within a blood vessel without significantly obstructing fluid flow through said blood vessel;
    the pore size of the membrane being sufficient to allow plasma to diffuse through the pores but not sufficient to allow cellular components larger than plasma to diffuse therethrough, so as to accomplish in vivo separation of plasma from blood;
    plasma collection means in fluid communication with the membrane and having a hollow tube which conducts plasma from the primary filter;
    extracorporeal analytical means connected to receive the plasma passing through the tube and operative to measure a blood gas parameter of the plasma; and
    means conducting the plasma from the extracorporeal analytical means for return to a blood vessel.

13. A method for measuring at least one parameter of blood flowing in an organism, comprising the steps of:
    implanting in a blood vessel at least one elongated microporous fiber having a hollow interior and dimensioned to be received within a blood vessel without significantly obstructing fluid flow through the blood vessel, the pore size of the elongated microporous fiber being sufficient to allow plasma to diffuse through the pores into the hollow interior of the fiber but not sufficient to allow cellular components larger than plasma to diffuse therethrough, so as to accomplish in vivo separation of plasma from blood;

placing the hollow interior of said elongated fiber in fluid communication with a means for conducting plasma comprising a first hollow tube which connects to the hollow interior of the fiber and permits passage of plasma from the fiber, and a second discrete tube which returns plasma to said blood vessel;

removing plasma from the blood vessel to an extracorporeal location;

analyzing the removed plasma at the extracorporeal location to determine at least one blood parameter from the plasma; and then re-infusing the plasma into the blood vessel.

14. A method for measuring at least one parameter of blood using plasma in lieu of blood, comprising the steps of:

separating plasma from blood in vivo in a blood vessel;

removing the separated plasma from the blood vessel to an extracorporeal location;

analyzing the removed plasma at the extracorporeal location to determine at least one blood parameter from the plasma; and then re-infusing the plasma into the blood vessel.

* * * * *